(12) United States Patent
Sudo et al.

(10) Patent No.: US 9,499,543 B2
(45) Date of Patent: Nov. 22, 2016

(54) POLYMORPH FORMS

(71) Applicant: RaQualia Pharma Inc., Aichi (JP)

(72) Inventors: Masaki Sudo, Aichi (JP); Kaoru Shimada, Aichi (JP); Hiroaki Wakabayashi, Aichi (JP); Toyoharu Numata, Aichi (JP)

(73) Assignee: RaQualia Pharma Inc., Aichi (JP)

( * ) Notice: Subject to any disclaimer, the term of this patent is extended or adjusted under 35 U.S.C. 154(b) by 0 days.

(21) Appl. No.: 14/890,678

(22) PCT Filed: May 28, 2014

(86) PCT No.: PCT/JP2014/002819
§ 371 (c)(1),
(2) Date: Nov. 12, 2015

(87) PCT Pub. No.: WO2014/192294
PCT Pub. Date: Dec. 4, 2014

(65) Prior Publication Data
US 2016/0083381 A1 Mar. 24, 2016

Related U.S. Application Data

(60) Provisional application No. 61/827,958, filed on May 28, 2013.

(51) Int. Cl.
*A61K 31/437* (2006.01)
*C07D 471/04* (2006.01)
*A61K 31/4162* (2006.01)
*C07C 59/255* (2006.01)

(52) U.S. Cl.
CPC ......... *C07D 471/04* (2013.01); *A61K 31/4162* (2013.01); *A61K 31/437* (2013.01); *C07C 59/255* (2013.01); *C07B 2200/13* (2013.01)

(58) Field of Classification Search
CPC .......... A61K 31/4162; A61K 31/437; C07D 471/04
USPC ........................................................ 514/303
See application file for complete search history.

(56) References Cited

U.S. PATENT DOCUMENTS

2002/0002283 A1 1/2002 Busch et al.
2002/0049196 A1 4/2002 Carpino et al.

FOREIGN PATENT DOCUMENTS

| CN | 1152049 C | 6/2004 |
|----|-----------|--------|
| EP | 1 031 575 | 8/2000 |
| JP | 11-501945 | 2/1999 |
| JP | 2000-247974 | 9/2000 |
| WO | 97/24369 | 7/1997 |

(Continued)

OTHER PUBLICATIONS

International Search Report issued Jun. 24, 2014 in International Application No. PCT/JP2014/002819.

(Continued)

*Primary Examiner* — Kamal Saeed
*Assistant Examiner* — Janet L Coppins
(74) *Attorney, Agent, or Firm* — Wenderoth, Lind & Ponack, L.L.P.

(57) ABSTRACT

The present invention relates to novel crystal forms of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate. More particularly, the invention relates to polymorph forms, and to processes for the preparation of compositions containing and to uses of such polymorph forms.

8 Claims, 1 Drawing Sheet

(56) References Cited

FOREIGN PATENT DOCUMENTS

WO WO 9724369 A1 * 7/1997 ............ C07D 471/04
WO 98/58949 12/1998

OTHER PUBLICATIONS

Written Opinion of the International Searching Authority issued Jun. 24, 2014 in International Application No. PCT/JP2014/002819.

Byrn, S. et al., "Pharmaceutical Solids: A Strategic Approach to Regulatory Considerations", Pharmaceutical Research, vol. 12, No. 7, 1995, pp. 945-954.

Bavin, M., "Polymorphism in Process Development", Chemistry & Industry, 1989, (16), pp. 527-529.

Tokunaga, T., et al. "Oxindole Derivatives as Orally Active Potent Growth Hormone Secretagogues", J. Med. Chem., 2001, 44(26), pp. 4641-4649.

* cited by examiner

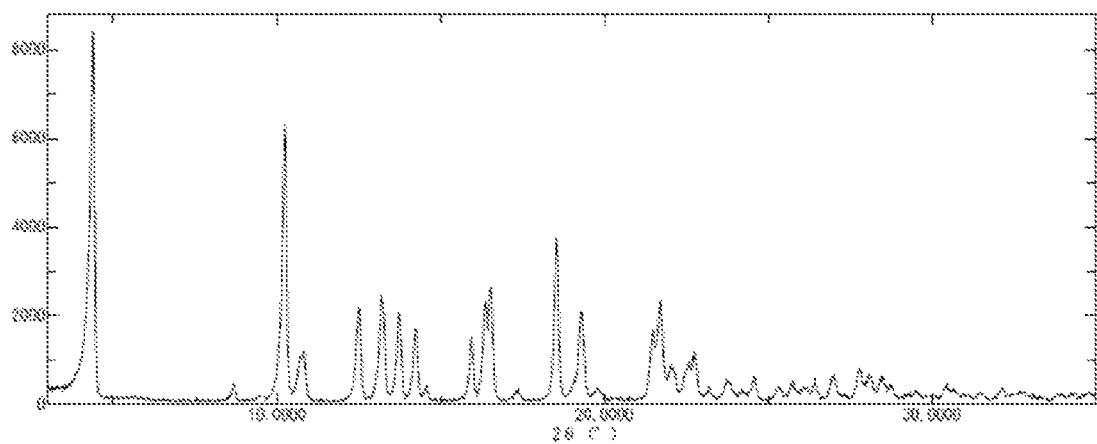

POLYMORPH FORMS

TECHNICAL FIELD

The present invention relates to novel crystal forms of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide.

More particularly, the invention relates to polymorph forms of the L-tartrate salt of the compound, and to processes for the preparation of, compositions containing and to uses of, such polymorphs.

BACKGROUND ART

The compound 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide is disclosed in WO97/024369 as a growth hormone secretagogue and a ghrelin receptor agonistic activity. The compound is named capromorelin and has been developed in the clinical stages. The synthetic process of the compound is also disclosed in EP-1031575.

However, neither a crystal nor mixture of other crystal forms of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide, have been known to the public.

CITATION LIST

Patent Literature

{PL 1} WO97/024369.
{PL 2} EP-1031575.

SUMMARY OF INVENTION

Technical Problem

As well-known by skilled in the art, it has been a desirable goal to find or prepare a crystalline or crystalline form in drug development from the various viewpoints including formulation and manufacturing of the drug (See Byrn S. R. et al., Solid-State Chemistry of Drugs 2nd ed., pp 3-43 and 461-503, 1999, SSCI, Inc.).

According to the line, great efforts have been made to find or prepare a crystalline or crystalline form of
2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide since the said compound was disclosed in 1997 (WO97/024369) by Pfizer Inc., In spite of such great efforts, no pharmaceutically suitable crystalline forms of the said compound have been identified yet.

After an exhaustive and careful study, the inventors of the present invention have managed to find out a condition of preparing the crystalline, which can provide the long-awaited crystalline form (Polymorph Form I) of the said compound as L-tartrate salt.

As disclosed in the working example of the present invention, Polymorph Form I has been identified.

It is an object of this invention to provide pharmaceutically suitable crystalline forms of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide, which can be easily, economically and reproducibly prepared for use in a pharmaceutical formulation having consistent performance characteristics, which are unexpectedly excellent in for example filterability, ease in handling, ease in purity control, stability and non-hygroscopicity. Also it is an object of this invention to provide processes for the preparation of, compositions containing and uses of, such polymorph forms.

Solution to Problem

Thus, the invention provides:
[1]
2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate Polymorph Form I, which is characterized by a powder X-ray diffraction pattern (PXRD) obtained by irradiation with Cu—Kalfa (Cu—Ka) radiation which includes main peaks at 2-Theta° 4.4, 10.2, 12.5, 13.2, 13.7, 16.4, 16.6, 18.5, 19.3 and 21.7 +/−0.2;
[2]
2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate Polymorph Form I as described in [1], which is further characterized by differential scanning calorimetry (DSC) in which it exhibits an endothermic event at about 177° C.;
[3]
2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate Polymorph Form I as described in [1] or [2], which is further characterized by an infrared (IR) spectrum (KBr) which shows absorption bands at 3349, 3107, 3036, 2983, 2870, 2770, 2526, 1705, 1662, 1625, 1531, 1454, 1442, 1220, 1132, 1109, 1089, and 704 +/−2 cm$^{-1}$.
[4]
A pharmaceutical composition including 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate Polymorph Form I as described in any one of [1] to [3], together with one or more pharmaceutically acceptable excipients;
[5]
2-amino-N-[2-(3a-(R)-benzyl-2-methyl-3-oxo-2,3,3a,-4,6,7-hexahydro-pyrazolo[4,3-c]pyridin-5-yl)-1-(R)-benzyloxymethyl-2-oxo-ethyl]-isobutyramide L-tartrate Polymorph Form I as described in any one of [1] to [3] for use as a medicament;
[6]
The use of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate Polymorph Form I as described in any one of [1] to [3], or a pharmaceutical composition as described in [4], in the preparation of a medicament for the curative, palliative or prophylactic treatment of disease conditions mediated by a ghrelin receptor agonistic activity;
[7]
A method of treating disease conditions mediated by a ghrelin receptor activity, which comprises administering an effective amount of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate Polymorph Form I as described in any one of [1] to [3], or a pharmaceutical composition as described in [4], to an animal, including a human, in need of such treatment;

[8]
A process for preparing 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate Polymorph Form I as described in [1] to [3], comprising the step of exposing 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide in an organic solvent, preferably ethyl acetate under the condition of L-tartaric acid in alcohol, preferably methyl alcohol, ethyl alcohol and isopropyl alcohol, more preferably methyl alcohol and isopropyl alcohol;

[9]
A process for preparing 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate Polymorph Form I as described in any one of [1] to [3], comprising the step of exposing 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide in ethyl acetate under the condition of L-tartaric acid in methanol or isopropyl alcohol.

[10]
A process for preparing 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate Polymorph Form I as described in any one of [1] to [3], comprising the step of exposing 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide to an alcohol selected from methyl alcohol, ethyl alcohol and isopropyl alcohol.

[11]
The process for preparing 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate Polymorph Form I as described in [10], comprising the step of exposing 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide to methanol or iso-propanol.

Advantageous Effects of Invention

As mentioned above, it is an object of the present invention to find or prepare a crystalline or crystalline form having unexpectedly excellent physicochemical characteristics for drug development from the various viewpoints including formulation and manufacturing of the drug. It has now been surprisingly found that this object has been achieved by the present invention, which provides crystalline polymorphic forms of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate named as Polymorph Form I.

No pharmaceutically suitable crystalline forms of the said compound have been identified in spite of great efforts of those skilled in the art.

All of the polymorphs of the present invention have an excellent and unexpected advantage over the white solid disclosed in the prior art WO97/024369. Polymorph Form I is found to be more stable than the solid disclosed in the prior art WO97/024369.

Furthermore Polymorph Forms of the present invention are found to be applicable for a large scale synthesis. They have acceptable solid-state properties for solid-dosage form development.

BRIEF DESCRIPTION OF DRAWINGS

FIG. 1 shows the PXRD pattern of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate Polymorph Form I.

DESCRIPTION OF EMBODIMENTS

Accordingly, the present invention provides crystalline 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate Polymorph Form I, which is characterized by a powder X-ray diffraction pattern (PXRD) obtained by irradiation with Cu-Ka radiation which includes main peaks at 2-Theta° 4.4, 10.2, 12.5, 13.2, 13.7, 16.4, 16.6, 18.5, 19.3 and 21.7 +/−0.2;

2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate Polymorph Form I as described above, which is further characterized by differential scanning calorimetry (DSC) in which it exhibits an endothermic thermal event at about 177° C.;

Polymorph Form I as described above, which is yet further characterized by an infrared (IR) spectrum (KBr) which shows absorption bands at 3349, 3107, 3036, 2983, 2870, 2770, 2526, 1705, 1662, 1625, 1531, 1454, 1442, 1220, 1132, 1109, 1089, and 704 +/−2 $cm^{-1}$;

As a further aspect of the invention, there is provided 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate Polymorph Form I of the present invention for use as a medicament.

As a yet further aspect of the invention, there is provided the use of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate Polymorph Form I of the present invention in the manufacture of a medicament for the treatment of any disease for which a ghrelin receptor agonist is indicated, particularly for the curative, prophylactic or palliative treatment of 1) a gastrointestinal disorder, 2) a disorder characterized by lack of appetite, suppressed appetite, or that results in decreased food intake, and 3) a disease in which high gastric acid secretion is involved.

The gastrointestinal disorder can be selected from the group consisting of post-operative ileus, gastroparesis, opioid-induced bowel dysfunction, chronic intestinal pseudo-obstruction, acute colonic pseudo-obstruction (Ogilvie's syndrome), enteric dysmotility, short bowel syndrome, emesis, constipation-predominant irritable bowel syndrome (IBS), chronic constipation, functional dyspepsia, cancer-associated dyspepsia syndrome, graft versus host disease, delayed gastric emptying, gastrointestinal dysfunction or delayed gastric emptying occurring in conjunction with other disease states, gastrointestinal dysmotility or delayed gastric emptying occurring in critical care situations, gastrointestinal dysfunction or delayed gastric emptying as a result of treatment with pharmaceutical agents, gastroesophageal reflux disease (GERD), gastric ulcers, gastroenteritis and Crohn's disease.

The disorder characterized by lack of appetite, suppressed appetite, or that results in decreased food intake can be cachexia, wherein cachexia is induced by cancer, chronic heart failure, acquired immunodeficiency syndrome (AIDS), renal disease, muscular dystrophies or aging.

The disease in which high gastric acid secretion is involved can be achlorhydria.

As an alternative aspect, there is provided a method for the treatment of any disease for which a ghrelin receptor agonist is indicated, particularly for the curative, prophylactic or palliative treatment of 1) a gastrointestinal disorder, 2) a disorder characterized by lack of appetite, suppressed appetite, or that results in decreased food intake, and 3) a disease in which high gastric acid secretion is involved, including administration of a therapeutically effective amount of 2-amino-N-[2-(3a-(R)-benzyl-2-methyl-3-oxo-2, 3,3a,4,6,7-hexahydro-pyrazolo[4,3-c]pyridin-5-yl)-1-(R)-benzyloxymethyl-2-oxo-ethyl]-isobutyramide L-tartrate Polymorph Form I of the present invention to an animal, including a human, in need of such treatment.

The 2-amino-N-[2-(3a-(R)-benzyl-2-methyl-3-oxo-2,3, 3a,4,6,7-hexahydro-pyrazolo[4,3-c]pyridin-5-yl)-1-(R)-benzyloxymethyl-2-oxo-ethyl]-isobutyramide L-tartrate Polymorph Form I of the present invention is useful for the general treatment of disease conditions mediated by ghrelin receptor agonistic activity.

The 2-amino-N-[2-(3a-(R)-benzyl-2-methyl-3-oxo-2,3, 3a,4,6,7-hexahydro-pyrazolo[4,3-c]pyridin-5-yl)-1-(R)-benzyloxymethyl-2-oxo-ethyl]-isobutyramide L-tartrate Polymorph Form I of the present invention can also be useful for the treatment of a disorder or condition selected from the group consisting of 1) a gastrointestinal disorder, 2) a disorder characterized by lack of appetite, suppressed appetite, or that results in decreased food intake, and 3) a disease in which high gastric acid secretion is involved.

Synthetic routes for the preparation of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide are described in WO97/024369 and in Example Section below.

The 2-amino-N-[2-(3a-(R)-benzyl-2-methyl-3-oxo-2,3, 3a,4,6,7-hexahydro-pyrazolo[4,3-c]pyridin-5-yl)-1-(R)-benzyloxymethyl-2-oxo-ethyl]-isobutyramide L-tartrate Polymorph Form I can be prepared by crystallization from a solution of
2-amino-N-[2-(3a-(R)-benzyl-2-methyl-3-oxo-2,3,3a,4,6, 7-hexahydro-pyrazolo[4,3-c]pyridin-5-yl)-1-(R)-benzyloxymethyl-2-oxo-ethyl]-isobutyramide in an organic solvent such as ethyl acetate by adding an alcohol such as a methyl alcohol solution of L-tartrate.

Organic solvents including carboxylic ester such as ethyl acetate and alcohol such as methyl alcohol, ethyl alcohol and isopropyl alcohol can be used for the crystallization of Polymorph Form I.

The 2-amino-N-[2-(3a-(R)-benzyl-2-methyl-3-oxo-2,3, 3a,4,6,7-hexahydro-pyrazolo[4,3-c]pyridin-5-yl)-1-(R)-benzyloxymethyl-2-oxo-ethyl]-isobutyramide L-tartrate Polymorph Form I of the present invention can be administered alone or in combination with one or more other drugs (or as any combination thereof). Generally, they will be administered as a formulation in association with one or more pharmaceutically acceptable excipients. The term 'excipient' is used herein to describe any ingredient other than the compound of the invention. The choice of excipient will to a large extent depend on factors such as the particular mode of administration, the effect of the excipient on solubility and stability, and the nature of the dosage form.

Thus, as a further aspect of the present invention, there is provided a pharmaceutical composition including
2-amino-N-[2-(3a-(R)-benzyl-2-methyl-3-oxo-2,3,3a,4,6, 7-hexahydro-pyrazolo[4,3-c]pyridin-5-yl)-1-(R)-benzyloxymethyl-2-oxo-ethyl]-isobutyramide L-tartrate Polymorph Form I and one or more suitable excipients. The composition is suitable for the treatment of disease conditions mediated by a ghrelin receptor activity.

Weight purity of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate Polymorph Form I of the present invention is not limited, but preferably an essentially pure Polymorph Form can be used for specific embodiments in this invention.

For the avoidance of doubt, the expression 'essentially pure' when used herein means at least 90% by weight purity. More preferably, 'essentially pure' means at least 95% by weight purity and most preferably means at least 98% by weight purity. References herein to "treatment" include references to curative, palliative and prophylactic treatment.

For non-human animal administration, the term 'pharmaceutical' as used herein may be replaced by 'veterinary.'

Pharmaceutical compositions suitable for the delivery of Polymorph Form of the invention and methods for the preparation will be readily apparent to those skilled in the art. Such compositions and methods for the preparation may be found, for example, in Remington's Pharmaceutical Sciences, 19th Edition (Mack Publishing Company, 1995); Polymorphism: In the Pharmaceutical Industry by Rolf Hilfiker (John Wiley & Sons, 2006).

Oral Administration

Polymorph Form I of the invention may be administered orally. Oral administration may involve swallowing, so that the compound enters the gastrointestinal tract, and/or buccal, lingual, or sublingual administration by which the compound enters the blood stream directly from the mouth.

Formulations suitable for oral administration include solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccal or mucoadhesive patches.

Liquid formulations include suspensions, solutions, syrups and elixirs. Such formulations may be employed as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

Polymorph Form I of the invention may also be used in fast-dissolving, fast-disintegrating dosage forms such as those described in Expert Opinion in Therapeutic Patents, 11(6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate.

Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may be contained from 0.2 weight % to 5 weight % of the tablet, and glidants may be contained from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in Pharmaceutical Dosage Forms: Tablets, Vol. 1, by H. Lieberman and L. Lachman (Marcel Dekker, New York, 1980); Pharmaceutical Dosage Forms: Tablets, Third Edition, Volume 2: Rational Design and Formulation, by Larry L. Augsburger and Hoag W. Stephen (Informa Healthcare, Published June 2008).

Consumable oral films for human or veterinary use are typically pliable water-soluble or water-swellable thin film dosage forms which may be rapidly dissolving or mucoadhesive and typically comprise a Polymorph Form in accordance with the invention, a film-forming polymer, a binder, a solvent, a humectant, a plasticizer, a stabilizer or emulsifier, a viscosity-modifying agent and a solvent. Some components of the formulation may perform more than one function.

Polymorph Form I of the invention may be water-soluble or insoluble. A water-soluble compound typically may be contained from 1 weight % to 80 weight %, more typically from 20 weight % to 50 weight %, of the solutes. Less soluble compounds may be contained in a greater proportion of the composition, typically up to 88 weight % of the solutes. Alternatively, Polymorph Form I of the invention may be in the form of multiparticulate beads.

The film-forming polymer may be selected from natural polysaccharides, proteins, or synthetic hydrocolloids and is typically present in the range of 0.01 to 99 weight %, more typically in the range of 30 to 80 weight %.

Other possible ingredients include anti-oxidants, colorants, flavourings and flavour enhancers, preservatives, salivary stimulating agents, cooling agents, co- solvents (including oils), emollients, bulking agents, anti-foaming agents, surfactants and taste-masking agents.

Films in accordance with the invention are typically prepared by evaporative drying of thin aqueous films coated onto a peelable backing support or paper.

This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in Pharmaceutical Technology On-line, 25(2), 1-14, by Verma et al (2001). The use of chewing gum to achieve controlled release is described in WO 00/35298.

Parenteral Administration

The Polymorph Form I of the invention may also be administered directly into the blood stream, into muscle, or into an internal organ. Suitable means for parenteral administration include intravenous, intraarterial, intraperitoneal, intrathecal, intraventricular, intraurethral, intrastemal, intracranial, intramuscular, intrasynovial and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilization, may readily be accomplished using standard pharmaceutical techniques well known to those skilled in the art.

Formulations for parenteral administration may be formulated to be immediate and/or modified release. Modified release formulations include delayed-, sustained-, pulsed-, controlled-, targeted and programmed release. Thus the Polymorph Form I of the invention may be formulated as a suspension or as a solid, semi-solid, or thixotropic liquid for administration as an implanted depot providing modified release of the active compound. Examples of such formulations include drug-coated stents and semi-solids and suspensions comprising drug-loaded poly(lactic-co-glycolic acid) (PLGA) microspheres.

Topical Administration

The Polymorph Form I of the invention may also be administered topically, (intra)dermally, or transdermally to the skin or mucosa. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958, by Finnin and Morgan (October 1999).

Other means of topical administration include delivery by electroporation, iontophoresis, phonophoresis, sonophoresis and microneedle or needle-free (e.g. Powderject (trade mark), Bioject (trade mark), etc.) injection. Topical administration may also be achieved using a patch, such as a transdermal iontophoretic patch.

Formulations for topical administration may be formulated to be immediate and/or modified release. Modified release formulations include delayed-, sustained-, pulsed-, controlled-, targeted and programmed release.

The Polymorph Form I of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler, as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane, or as nasal drops. For intranasal use, the powder may comprise a bioadhesive agent, for example, chitosan or cyclodextrin.

The pressurized container, pump, spray, atomizer, or nebulizer contains a solution or suspension of a Polymorph Form in accordance with the invention comprising, for example, ethanol, aqueous ethanol, or a suitable alternative agent for dispersing, solubilizing, or extending release of the active, a propellant(s) as solvent and an optional surfactant, such as sorbitan trioleate, oleic acid, or an oligolactic acid.

Prior to use in a dry powder or suspension formulation, the drug product is micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as /-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomizer using electrohydrodynamics to produce a fine mist may contain from 1 micro g to 20 mg of the compound of the invention per actuation and the actuation volume may vary from 1 micro L to 100 micro L. A typical formulation may comprise a Polymorph Form in accordance with the invention, propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, PLGA. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from 1 micro g to 20 mg of 2-amino-N-[2-(3a-(R)-benzyl-2-methyl-3-oxo-2,3,3a,4,6,7-hexahydro-pyrazolo[4,3-c]pyridin-5-yl]-1-(R)-benzyloxymethyl-2-oxo-ethyl]-isobutyramide L-tartrate Polymorph Form I. The overall daily dose will typically be in the range of 1 micro g to 100 mg which may be administered in a single dose or, more usually, as divided doses throughout the day.

Rectal/Intravaginal Administration

Polymorph Form I of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

Ocular/Aural Administration

Polymorph Form I of the invention may also be administered directly to the eye or ear, typically in the form of drops of a micronized suspension or solution in isotonic, pH-adjusted, sterile saline. Other formulations suitable for ocular and aural administration include ointments, gels, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gellan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

Other Technologies

Polymorph Form I of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubilizer. Most commonly used for these purposes are alpha-, beta- and gamma-cyclodextrins, examples of which may be found in International Patent Applications Nos. WO 91/11172, WO 94/02518, WO 98/55148 and Evrard, B.,et al., Journal of Controlled Release 96 (3), pp. 403-410, 2004.

Dosage

For treating or preventing the disease conditions mediated by a ghrelin receptor activity, a suitable dosage level of Polymorph Form I of this invention is about 0.0001 to 1000 mg per day, preferably about 0.001 to 100 mg per day, and more preferably about 0.005 to 50 mg per day, and most preferably 1 to 50 mg per day of the active compound. The compounds may be administered on a regimen of 1 to 4 times per day. In some cases, however, a dosage outside these limits may be used.

These dosages are based on an average human subject having a weight of about 60 kg to 70 kg. The physician will readily be able to determine doses for subjects whose weight falls outside this range, such as infants and the elderly. For the avoidance of doubt, references herein to "treatment" include references to curative, palliative and prophylactic treatment.

Polymorph Form I of the present invention may also optionally be combined with another pharmacologically active compound, or with two or more other pharmacologically active compounds, particularly for the treatment of disease conditions mediated by a ghrelin receptor activity. For example, the Polymorph Form I of the present invention, as defined above, may be administered simultaneously, sequentially or separately in combination with one or more agents selected from;

- an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;
- a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;
- a barbiturate sedative, e.g. amobarbital, aprobarbital, butabarbital, butalbital, mephobarbital, metharbital, methohexital, pentobarbital, phenobartital, secobarbital, talbutal, theamylal or thiopental;
- a benzodiazepine having a sedative action, e.g. chlordiazepoxide, clorazepate, diazepam, flurazepam, lorazepam, oxazepam, temazepam or triazolam;
- an H1 antagonist having a sedative action, e.g. diphenhydramine, pyrilamine, promethazine, chlorpheniramine or chlorcyclizine;
- a sedative such as glutethimide, meprobamate, methaqualone or dichloralphenazone;
- a skeletal muscle relaxant, e.g. baclofen, carisoprodol, chlorzoxazone, cyclobenzaprine, methocarbamol or orphenadrine;
- an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex(registered trademark), a combination formulation of morphine and dextromethorphan), topiramate, neramexane or perzinfotel including an NR2B antagonist, e.g. ifenprodil, traxoprodil or (−)-(R)-6- {2- [4-(3-fluorophenyl)-4-hydroxy-l-piperidinyl]-1-hydroxyethyl-3,4-dihydro-2 (1H)-quinolinone;
- an alpha-adrenergic, e.g. doxazosin, tamsulosin, clonidine, guanfacine, dexmedetomidine, modafinil, or 4-amino-6,7-dimethoxy-2-(5-methane-sulfonamido-1, 2,3,4-tetrahydroisoquinol-2-yl)-5-(2-pyridyl) quinazoline;
- a tricyclic antidepressant, e.g. desipramine, imipramine, amitriptyline or nortriptyline;
- an anticonvulsant, e.g. carbamazepine, lamotrigine, topiratmate or valproate;
- a tachykinin (NK) antagonist, particularly an NK-3, NK-2 or NK-1 antagonist, e.g. alphaR,9R)-7-[3,5-bis(trifluoromethyl)benzyl]-8,9,10,11-tetrahydro-9-methyl-5-(4-met hylphenyl)-7H-[1,4]diazocino[2,1-g][1,7]-naphthyridine-6-13-dione (TAK-637), (the symbol "α" is written "alpha" herein the specification), 5-[[(2R,3S)-2-R1R)-1-[3,5-bis(trifluoromethyl)phenyl]ethoxy-3-(4-fluorophenyl)-4-morpholinyl]-methyl]-1,2-dihydro-3H-1,2,4-triazol-3-one(MK-869), aprepitant, lanepitant, dapitant or 3-[[2-methoxy-5-(trifluoromethoxy)phenyl]-methylamino]-2-phenylpiperidine (2S,3S);
- a muscarinic antagonist, e.g. oxybutynin, tolterodine, propiverine, trospium chloride, darifenacin, solifenacin, temiverine and ipratropium;
- a COX-2 selective inhibitor, e.g. celecoxib, rofecoxib, parecoxib, valdecoxib, deracoxib, etoricoxib, or lumiracoxib;
- a coal-tar analgesic, in particular paracetamol;
- a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion(registered trademark) or sarizotan;
- a vanilloid receptor agonist (e.g. resiniferatoxin) or antagonist (e.g. capsazepine);
- a transient receptor potential cation channel subtype (V1, V2, V3, V4, M8, A1) agonist or antagonist;
- a beta-adrenergic such as propranolol;
- a local anaesthetic such as mexiletine;
- a corticosteroid such as dexamethasone;
- a 5-HT receptor agonist or antagonist, particularly a 5-HT1B/1D agonist such as eletriptan, sumatriptan, naratriptan, zolmitriptan or rizatriptan;
- a 5-HT2A receptor antagonist such as R(+)-alpha-(2,3-dimethoxy-phenyl)-1-[2-(4-fluorophenylethyl)]-4-piperidinemethanol (MDL-100907);
- a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;
- Tramadol(registered trademark);
- a PDEV inhibitor, such as 5-[2-ethoxy-5-(4-methyl-1-piperazinyl-sulphonyl)phenyl]-1-methyl-3-n-propyl-1, 6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazino[2',1':6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4] triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d] pyrimidin-7-one, 5-[2-ethoxy-5-(4-ethylpiperazin-1- ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl)pyrrolidin-1-yl-]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

an alpha-2-delta ligand such as gabapentin, pregabalin, 3-methylgabapentin, (1alpha,3 alpha,5alpha)(3-aminomethyl-bicyclo[3.2.0]hept-3-yl)-acetic acid, (3S,5R)-3 aminomethyl-5 methyl-heptanoic acid, (3S,5R)-3 amino-5 methyl-heptanoic acid, (3S,5R)-3 amino-5 methyl-octanoic acid, (2S,4S)-4-(3-chlorophenoxy) proline, (2S,4S)-4-(3-fluorobenzyl)-proline, [(1R,5R, 6S)-6-(aminomethyl)bicyclo[3.2.0]hept-6-yl]acetic acid, 3-(1-aminomethyl-cyclohexylmethyl)-4H-[1,2,4] oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3 aminomethyl-5 methyl-octanoic acid, (3S,5R)-3 amino-5 methyl-nonanoic acid, (3S,5R)-3 amino-5 methyl-octanoic acid, (3R,4R,5R)-3-amino-4,5-dimethyl-heptanoic acid and (3R,4R,5R)-3-amino-4,5-dimethyl-octanoic acid;

a cannabinoid;

a metabotropic glutamate subtype 1 receptor (mGluR1) antagonist;

a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;

a noradrenaline (norepinephrine) reuptake inhibitor, such as maprotiline, lofepramine, mirtazapine, oxaprotiline, fezolamine, tomoxetine, mianserin, buproprion, buproprion metabolite hydroxybuproprion, nomifensine and viloxazine (Vivalan (registered trademark)), especially a selective noradrenaline reuptake inhibitor such as reboxetine, in particular (S,S)-reboxetine;

a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran and imipramine;

an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl) amino]-5-heptenoic acid, 2-[[(1R,3S)-3-amino-4-hydroxy-1-(5-thiazolyl)-butyl]thio]-5-chloro-3-pyridinecarbonitrile; 2-[[(1R,3S)-3-amino-4-hydroxy-1-(5-thiazolyl)butyl]thio]-4-chlorobenzonitrile, (2S, 4R)-2-amino-4-[[2-chloro-5-(trifluoromethyl)phenyl] thio]-5-thiazolebutanol, 2-[[(1R,3S)-3-amino-4-hydroxy-1-(5-thiazolyl)butyl]thio]-6-(trifluoromethyl)-3 pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino) ethyl]phenyl]thiophene-2-carboxamidine, or guanidinoethyldisulfide;

an acetylcholinesterase inhibitor such as donepezil;

a prostaglandin E2 subtype 4 (EP4) antagonist such as N-[({2-[4-(2-ethyl-4,6-dimethyl-1H-imidazo[4,5-c] pyridin-1-yl)phenyl]ethyl }amino)-carbonyl]-4-methylbenzenesulfonamide or 4-[(1S)-1-({[5-chloro-2-(3-fluorophenoxy)pyridin-3-yl]carbonyl } amino)ethyl] benzoic acid;

a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870, a 5-lipoxygenase inhibitor, such as zileuton, 6-[(3-fluoro-5-[4-methoxy-3,4,5,6-tetrahydro-2H-pyran-4-yl])phenoxy-methyl]-1-methyl-2-quinolone (ZD-2138), or 2,3,5-trimethyl-6-(3-pyridylmethyl),1,4-benzoquinone (CV-6504);

a sodium channel blocker, such as lidocaine;

a calcium channel blocker, such as ziconotide, zonisamide, mibefradil;

a 5-HT3 antagonist, such as ondansetron;

a chemotherapy drug such as oxaliplatin, 5-fluorouracil, leukovolin, paclitaxel;

a calcitonin gene related peptide (CGRP) antagonist;

a bradykinin (BK1 and BK2) antagonist;

a voltage gated sodium dependent channel blocker ($Na_{v1.3}$, $Na_{v1.7}$, $Na_{v1.8}$);

a voltage dependent calcium channel blocker (N-type, T-type);

a P2X (ion channel type ATP receptor) antagonist;

an acid-sensing ion channel (ASIC1a, ASIC3) antagonist;

an Angiotensin AT2 antagonist;

a Chemokine CCR2B receptor antagonist;

a Cathepsin (B, S, K) inhibitor;

a sigma1 receptor agonist or antagonist;

and the pharmaceutically acceptable salts and solvates thereof.

Such combinations offer significant advantages, including synergistic activity, in therapy.

Combination Drug and Kit

One embodiment of the present invention is a combination of Polymorph Form of the present invention, and a drug for diseases, which is different from polymorph form of the present invention. A "combination" according to the invention may be present as a "fix combination" or as a "kit of parts combination". A "fix combination" is defined as a combination wherein the (i) at least one drug for diseases, which is different from Polymorph form I of the present invention, and (ii) Polymorph Form I is present in one unit. A "kit of parts combination" is defined as a combination wherein the (i) at least one drug for diseases, which is different from polymorph form of the present invention, and (ii) Polymorph Form I is present in more than one unit. The components of the "kit of parts combination" may be administered simultaneously, sequentially or separately. The molar ratio of the drug, which is different from polymorph form of the present invention, to Polymorph Form used according to the invention is within the range of from 1:100 to 100:1, such as from 1:50 to 50:1 or from 1:20 to 20:1 or from 1:10 to 10:1. The two drugs may be administered separately in the same ratio.

The present invention extends to a combination comprising 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate Polymorph Form I and one or more therapeutic agents, such as those listed above, for simultaneous, separate or sequential use in the curative, prophylactic or palliative treatment of disease conditions mediated by a ghrelin receptor activity.

EXAMPLES

The following example is for reference only.
Analysis
Powder X-Ray Diffraction (PXRD)

The PXRD analyses are performed using a Rigaku RINT-TTR X-ray powder diffractometer using Cu—Kα radiation. The samples can also be measured under the high/low temperature condition by using the attachment of the variant-temperature sample holder. The instrument is equipped with a fine focus X-ray tube. The tube voltage and amperage are set to 50 kV and 300 mA respectively. The divergence and scattering slits are set at 0.5° and the receiving slit is set at 0.15 mm. Diffracted radiation is detected by a NaI scintillation detector. A theta-two theta continuous scan at 4°/min (step size 0.02°) from 3 to 40 2-Theta° is used. A silicon standard is analyzed to check the machine alignment. Data are collected and analyzed using-Rigaku X-ray system. Samples are prepared for analysis by placing them in an aluminum sample holder that is horizontally rotated at 60 rpm during data acquisition.

Thermogravimetry/differential Thermal Analysis (TG/DTA)

TG/DTA is performed using Seiko 6200R system. The sample is placed into an aluminum TG/DTA pan. Each sample is heated under a nitrogen purge at a rate of 5° C./min, up to a final temperature of 300° C. Indium metal is used as the calibration standard. Reported values are rounded and should therefore be considered approximate.

Differential Scanning Calorimetry (DSC)

DSC analysis is performed using Mettler Toledo DSC822. The sample is placed into an aluminum DSC pan and the weight accurately recorded. The pan is covered with a lid with a pinhole and then crimped. Each sample is heated under a nitrogen purge at a rate of 5° C./min, up to a final temperature of 220° C. Indium metal is used as the calibration standard. Reported values are rounded and should therefore be considered approximate.

FT-IR Spectroscopy

Infrared spectra are acquired on a Shimadzu IRPrestage-21 (FT-IR) spectrophotometer equipped with a black-coated heated wire beam source, a Germanium coated on potassium bromide (KBr) beamsplitter, and a high sensitivity pyroelectric detector (DLATGS). Each spectrum represents 40 co-added scans collected at a spectral resolution of 4 $cm^{-1}$. Sample preparation consisted of placing the KBr disk, prepared from the sample and KBr. A background data set is acquired with a blank disk of KBr without samples. A Log MR (R=reflectance) spectrum is acquired by taking a ratio of these two data sets against each other. Wavelength calibration is performed using polystyrene. Reported values are rounded and should therefore be considered approximate.

Hygroscopicity study by dynamic vapor sorption analysis (DVS)

Hygroscopicity study is performed using Surface Measurement Systems DVS-1. The sample is placed on a microbalance in the instrument and the weight change during the sorption/desorption cycle at 25° C. is monitored. One of the sorption/desorption programs consists of a sorption scan from 0 to 95% relative humidity (RH) and a desorption scan from 95 to 10% RH. The other consists of a sorption scan from 40 to 95% RH and desorption scan from 95 to 0% RH, followed by a second sorption scan from 0 to 40% RH. Both programs are carried out at 5% RH increments and the sample is allowed to equilibrate for 360 minutes or until equilibration had been attained at each step. At the end of the DVS experiment the sample is measured by PXRD.

Nuclear Magnetic Resonance (NMR)

NMR data are determined at 270 MHz (JEOL JNM-LA 270 spectrometer) or 300 MHz (JEOL JNM-LA300) using deuterated chloroform (99.8% D) or dimethyl-sulfoxide (99.9% D) as solvent unless indicated otherwise, relative to tetram-ethylsilane (TMS) as internal standard in parts per million (ppm); conventional abbreviations used are: s=singlet, d=doublet, t=triplet, q=quartet, m=multiplet, br=broad, etc.

High Performance Liquid Chromatography (HPLC) measurement

HPLC data are obtained by Waters Alliance 2695 HPLC system with 2996 PDA detector using the following conditions;

Column: lnertsil ODS-3 (3 μm, 4.6×150 mm),
Eluent: acetonitrile/10 mM ammonium acetate=32:68,
Detection: UV at 215 nm,
Flow rate: 1 mL/min, and
Column temperature: 40° C.
Data processing is performed with Empower 2 software supplied from Waters Corporation.

Chemical symbols have their usual meanings; M (mol(s) per liter), L(liter(s)), mL (milliliter(s)), g (gram(s)), mg (milligram(s)), mol (moles), mmol (millimoles).

Example 1

Preparation of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide This compound is synthesized according to the conventional process described in WO97/024369.

Example 2

Preparation of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide This compound is synthesized according to the conventional process described in EP-1031575.

Example 3

Preparation of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate Polymorph Form I A mixture of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide obtained according to the method of EXAMPLE 1 (1.0 molar equivalents) is dissolved in ethyl acetate. The organic layer is extracted with purified water and/or filtered. A solution of L-tartaric acid (1.0 molar equivalents) in methanol is added and mixed. The solution is heated and the methanol/ethyl acetate is removed by distillation. Isopropanol is added and the solution is heated at reflux to obtain the desired polymorph conversion. The solids are isolated, washed, and dried in vacuo to yield the title compound salt.

Using a solution of L-tartaric acid in isopropanol instead of methanol gives the same crystal characterized below.

m.p. (DSC onset): 177° C.

Crystallinity by PXRD: Crystal (FIG. 1). Main peaks at 2-Theta°: 4.4, 10.2, 12.5, 13.2, 13.7, 16.4, 16.6, 18.5, 19.3 and 21.7. Each peak has a margin of error of +/−0.2.

MS (FAB) m/z: 506 (M+H)$^+$ with additional peaks observed at m/z 421, 263, and 244.

IR (KBr): 3349, 3107, 3036, 2983, 2870, 2770, 2526, 1705, 1662, 1625, 1531, 1454, 1442, 1220, 1132, 1109, 1089, and 704 cm$^{-1}$.

Anal. Calcd for C28H35N5O4 C4H6O6: C, 58.6; H, 6.3; N, 10.7. Found: C, 58.6; H, 6.4; N, 10.8.

Example 4

[Hygroscopicity Study]

In the hygroscopicity study by dynamic vapor sorption (DVS) analysis, Polymorph Form I shows good results (<2%) against moisture gain under 40%, 80%, and 90% relative humidity (RH) at 25 ° C. comparing with compound prepared in EXAMPLE 2.

Example 5

[Stability Study]

Solid-state stability study is performed using Nagano Science Constant temperature/ humidity control chamber LH-20-11M, LH-21-11M, LTL-200D3CJ-14 or LTX-01. The sample is placed in the chamber and exposed under 25° C./60% RH, 40° C./75% RH and/or irradiated with a Xenon lamp. The crystalline form, thermal behavior, purity and/or weight change of the resultant sample after the exposure or irradiation are evaluated by XRPD, TG/DTA or DSC, HPLC, microbalance, respectively.

Polymorph Form I is found to be stable comparing with compound prepared in EXAMPLE 2.

Example 6

[Solubility Study]

Polymorph Form I shows a good solubility (>300 mg/ml) in aqueous buffers below Ph 5.

Example 7

[Photostability Study]

Photostability samples are stored in open dishes with quartz glass covers and a second set of 25° C./60% RH, and 40° C./75% RH samples which are stored in open round amber glass bottles covered with gauze.

In summary, storing Polymorph Form I over 3 months, no significant changes are found in the appearance, the X-ray diffraction patterns, and IR spectra. No significant loss in potency is observed for any of the stability samples over 3 months.

The invention claimed is:

1. A Polymorphic Form I of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate, which is characterized by a powder X-ray diffraction pattern (PXRD) obtained by irradiation with Cu-Ka radiation having main peaks at 2-Theta of 4.4, 10.2,12.5, 13.2, 13.7, 16.4, 16.6, 18.5, 19.3 and 21.7 +/−0.2.

2. The Polymorphic Form I of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate according to claim 1, which is further characterized by differential scanning calorimetry (DSC) in which it exhibits an endothermic event at about 177° C.

3. The Polymorphic Form I of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate according to claim 1, which is further characterized by an infrared (IR) spectrum (KBr) having absorption bands at 3349, 3107, 3036, 2983, 2870, 2770, 2526, 1705, 1662, 1625, 1531, 1454, 1442, 1220, 1132, 1109, 1089, and 704 +/−2 cm−1.

4. A pharmaceutical composition in solid form comprising the Polymorphic Form I of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate according to claim 1, and at least one pharmaceutically acceptable excipient.

5. A method of treating disease condition mediated by a ghrelin receptor activity, wherein the disease condition is at least one selected from the group consisting of postoperative ileus, gastroparesis, opoid-induced bowel dysfunction, chronic intestinal pseudo-obstruction, acute colonic pseudeobstruction (Ogilvie's syndrome), enteric dysmotiliity, short bowel syndrome, emesis, constipation-predominant irritable bowel syndrome (IBS), chronic constipation, functional dyspepsia, cancer-associated dyspepsia syndrome, graft versus host disease, delayed gastric emptying, gastrointestinal dysfunction, gastrointestinal dysmotility, gastroesophageal reflux disease (GERD), gastric ulcers, gastroenteritis, Crohn's disease, cachexia and achlorhydria, which comprises administering an effective amount of the Polymorphic Form I of 2-amino-N-[2-(3a-(R)-benzyl-2-methyl-3-oxo-2, 3,3a,4,6,7-hexahydro-pyrazolo[4,3-c]pyridin-5-yl)-1-(R)-benzyloxymethyl-2-oxo-ethyl]isobutyramide L-tartrate according to claim 1 to an animal or a human in need of such treatment.

6. A process for preparing the Polymorphic Form I of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate according to claim 1, comprising dissolving a compound of 2amino-N-[2(3a-(R)-benzyl-2methyl-3-oxo-2,3a,4,6,7-hexahydro-pyrozolo[4,3c]pyrindin-5-yl-1-(R)-benzyloxymethyl-2-oxo-ethyl]-isobutyramide L-tartrate in an organic solvent and mixing with L-tartaric acid in an alcohol.

7. The process for preparing the Polymorphic Form I of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide L-tartrate according to claim 6, wherein the organic solvent is ethyl acetate, and the alcohol is selected from the group consisting of methyl alcohol, ethyl alcohol and isopropyl alcohol.

8. A method of treating a disease condition medicated by a ghrelin receptor activity, wherein the disease condition is at least one selected from the group consisting of postoperative ileus, gastroparesis, opioid-induced bowel dysfunction, chronic intestinal pseudo-obstruction, acute colonic pseudo-obstruction (Ogilvie's syndrome), enteric dysmotility, short bowel syndrome, enesis, constipation-predominant irritable bowel syndrome (IBS), chronic constipation, functional dyspepsia, cancer-associated dyspepsia syndrome, graft versus host disease, delayed gastric emptying, gastrointerstinal dysfunction, gastrointerstinal dysmotility, gastroesophageal reflux disease (GERD), gastric ulcer, gastroenteritis, Crohn's disease, cachexia and achlorhydria, which comprises administering an effective amount of the pharmaceutical composition according to claim 4 to an animal or a human in need of such treatment.

* * * * *

UNITED STATES PATENT AND TRADEMARK OFFICE
CERTIFICATE OF CORRECTION

PATENT NO. : 9,499,543 B2
APPLICATION NO. : 14/890678
DATED : November 22, 2016
INVENTOR(S) : Masaki Sudo It is certified that error appears in the above-identified patent and that said Letters Patent is hereby corrected as shown below:

In the Specification

Column 12, Lines 9-12 delete:
"alphaR,9R)-7-[3,5-bis(trifluoromethyl)benzyl]-8,9,10,11-tetrahydro-9-methyl-5-(4-met hylphenyl)-7H-[1,4]diazocino[2,1-g][1,7]-naph-thyridine-6-13-dione",
And insert:
--(alphaR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-dione--; and
Lines 13-16 delete:
"5-[[(2R,3S)-2-R1R)-1-[3,5-bis(trifluoromethyl)phenyl]ethoxy-3-(4-fluorophenyl)-4-morpholinyl]-methyl]-1,2-dihydro-3H-1,2,4-triazol-3-one(MK-869)",
And insert:
--5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869)--.

Column 14, Lines 13-14 delete:
"2,3,5-trimethyl-6-(3-pyridylmethyl),1,4-benzoquinone (CV-6504)",
And insert:
--2,3,5-trimethyl-6-(3-pyridylmethyl)-1,4-benzoquinone (CV-6504)--.

In the Claims

Claim 5, Column 18, Line 15 delete:
"treating disease",
And insert:
--treating a disease--;
Line 20 delete:
"enteric dysmotiliity",
And insert:
--enteric dysmotility--; and Signed and Sealed this
Sixth Day of February, 2018

Joseph Matal
*Performing the Functions and Duties of the
Under Secretary of Commerce for Intellectual Property and
Director of the United States Patent and Trademark Office*

Lines 29-31 delete:
"2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]isobutyramide",
And insert:
--2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide--.

Claim 6, Column 18, Lines 39-41 delete:
"2amino-N-[2(3a-(R)-benzyl-2methyl-3-oxo-2,3a,4,6,7-hexahydro-pyrozolo[4,3c]pyrindin-5-yl-1-(R)-benzyloxymethyl-2-oxo-ethyl]-isobutyramide L-tartrate",
And insert:
--2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide--.

Claim 8, Column 18, Line 50 delete:
"medicated",
And insert:
--mediated--;
Line 56 delete:
"enesis",
And insert:
--emesis--; and
Line 61 delete:
"ulcer",
And insert:
--ulcers--.